United States Patent [19]

Stark et al.

[11] Patent Number: 5,194,658
[45] Date of Patent: Mar. 16, 1993

[54] PROCESS FOR MAKING 2-AMINO-3-METHYL-1-NAPHTHALENECARBONITRILE

[75] Inventors: Edmund J. Stark; Duane B. Priddy, both of Midland, Mich.

[73] Assignee: The Dow Chemical Company, Midland, Mich.

[21] Appl. No.: 844,370

[22] Filed: Mar. 20, 1992

[51] Int. Cl.$^5$ ................. C07C 255/00; G01N 33/00
[52] U.S. Cl. ................... 558/418; 558/409; 558/431; 436/106; 436/111; 436/128
[58] Field of Search .................. 558/418, 409, 431

[56] References Cited

U.S. PATENT DOCUMENTS

| | | | |
|---|---|---|---|
| 2,032,465 | 3/1936 | Bradley et al. | 558/418 X |
| 3,423,412 | 1/1969 | Taylor et al. | 558/418 X |
| 3,514,458 | 5/1990 | Fields | 260/283 |
| 4,968,679 | 11/1990 | Junge et al. | 558/418 X |
| 5,035,736 | 7/1991 | Hageu et al. | 71/88 X |

OTHER PUBLICATIONS

Buzanowski et al., "The Spontaneous Polymerization of Styrene in the Presence of Acid: Further Confirmation of the Mayo Mechanism," Polymer Prepr., vol. 32(2), 220–221, (1991).
Kirchner et al., "The Formation of Oligomers in the Thermal Copolymerisation of the Styrene/Acrylonitrile-System," Makromol Chem., 177,2031–2042(1976).
E. J. Stark et al., "The Thermal Decomposition of Styrene-Co-Acrylonitrile Trimers to Form 2-Amino-3-Methyl-1-Napthalene–carbonitrile,"J. of Macromolecular Science: Macromolecular Reports, A29-(Supp. 1), pp. 1–11 (Apr. 1992).
Chemical Abstract 103:178024u (1985), Lan et al.
Chemical Abstracts 51:1917b (1957) Adams et al.
Derwent Abstract 88-089303/13 (1988) Toray.
Derwent Abstract 44882A/25 (1978) Mitsui.
Derwent Abstract 20065U/AE (1973) Imperial.

Primary Examiner—Floyd D. Higel

[57] ABSTRACT

2-amino-3-methyl-1-naphthalenecarbonitriles of the formula:

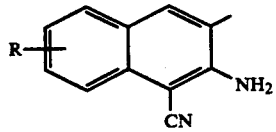

wherein R is alkyl of from 1 to 6 carbon atoms, halogen, cyano, or hydrogen are prepared by pyrolizing a by-product of a SAN or ABS manufacturing process of the formula:

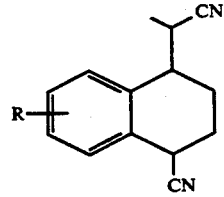

wherein R is alkyl of from 1 to 6 carbon atoms, halogen, cyano, or hydrogen.

In another respect, this invention is a process for identifying aldehydes comprising: (a) contacting 2-amino-3-methyl-1-naphthalene-carbonitrile with aldehydes to form an UV-absorbing imine, and (b) analyzing the imine using conventional analytical techniques to identify the presence of the imines.

5 Claims, No Drawings

PROCESS FOR MAKING 2-AMINO-3-METHYL-1-NAPHTHALENECARBONITRILE

BACKGROUND OF INVENTION

This invention relates to process for making aminonaphthalenecarbonitriles.

Copolymers of styrene and acrylonitrile are typically manufactured by mass polymerization processes. A by-product of such a process is 4-cyano-1,2,3,4-tetrahydro-α-methyl-1-napthaleneacetonitrile ("CTMNA"). CTMNA is represented by the formula:

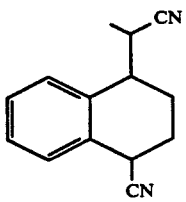

CTMNA is typically present in the styrene-acrylonitrile ("SAN") copolymer in an amount of from about one to about two percent by weight, but CTMNA is usually separated from the SAN copolymer such as by high temperature devolatilization. The CTMNA by-product is produced in other processes wherein styrene and acrylonitrile are polymerized, such as in the production of acrylonitrile-butadiene-styrene ("ABS") copolymers. Since there are millions of pounds of SAN and ABS copolymers produced worldwide, a tremendous amount of CTMNA is currently being produced. However, because CTMNA has heretofore found no commercial utility, it is disposed of such as by incineration. Accordingly, a need exists to find a use for CTMNA.

SUMMARY OF INVENTION

It has now been found that CTMNA or substituted CTMNA can be pyrolized to form 2-amino-3-methyl-1-naphthalenecarbonitrile ("AMNC") or substituted AMNC which can be represented by the formula:

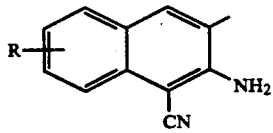

wherein R is alkyl of from 1 to 6 carbon atoms, halogen, cyano, or hydrogen.

AMNC or substituted AMNC find utility as tag reagents for analysis of aldehydes. This utility derives from AMNC being a fluorescent compound which reacts readily to form highly UV absorbing imine derivatives. Hence, this invention provides the conversion of a waste, CTMNA, into a new compound having high value as an analytical reagent. In addition, AMNC or substituted AMNC find utility as antagonistic agents for herbicides as shown in U.S. Pat. No. 5,035,736.

This invention, in one respect, is a process for producing AMNC or substituted AMNC, comprising heating CTMNA or substituted CTMNA represented by the formula:

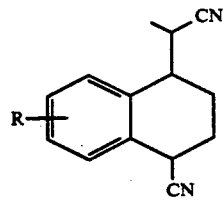

wherein R is alkyl of from 1 to 6 carbon atoms, halogen, cyano, or hydrogen under conditions effective to produce an AMNC or substituted AMNC and ethylene wherein AMNC or substituted AMNC is represented by the formula:

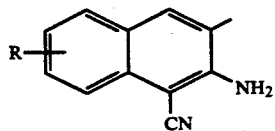

wherein R is alkyl of from 1 to 6 carbon atoms, halogen, cyano, or hydrogen.

In another respect, this invention is a process for identifying aldehydes comprising contacting 2-amino-3-methyl-1-naphthalenecarbonitrile with an aldehyde to form an UN-absorbing imine, and analyzing the imine using conventional analytical techniques to identify the presence of the imine.

DETAILED DESCRIPTION OF THE INVENTION

The starting material for production of AMNC or substituted AMNC is represented by the formula:

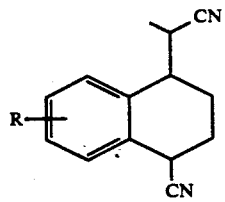

wherein R is alkyl of from 1 to 6 carbon atoms, halogen, cyano, or hydrogen. As used herein, the starting material is termed "CTMNA or substituted CTMNA." A halo substituent can be fluoro, chloro, bromo, or iodo. Most preferably, R is hydrogen. Starting material can be made by reaction of styrene or substituted styrene and acrylonitrile, such as in the manufacture of SAN and ABS copolymers. In the case of the manufacture of SAN copolymers, CTMNA or substituted CTMNA of this invention can be recovered using conventional separation techniques. Substituted styrene suitable for the production of AMNC or substituted derivatives thereof can be represented by the formula:

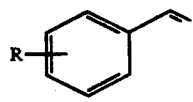

wherein R is as defined above.

CTMNA or substituted CTMNA can be converted to AMNC or substituted AMNC by pyrolysis. The pyrolysis can be run batch wise, such as in a sealed, evacuated ampoule or in an open vessel under an inert atmosphere. Examples of suitable inert gases that can be used to form the inert atmosphere are nitrogen, carbon dioxide, helium, and argon. The temperature of the pyrolysis is generally greater than about 200° C., preferably greater than about 250° C. Temperature is generally less than about 500° C., preferably less than about 350° C. Pressure can be atmospheric, superatmospheric, or subatmospheric. A solvent can be employed having a boiling point greater than or equal to the temperature at which the pyrolysis is to be carried out with the caveat that a lower boiling solvent can be employed if superatmospheric pressures are used. Examples of suitable solvents are halogenated benzenes such as trichlorobenzene, and diphenyloxide. The process is carried out for sufficient time to convert at least a portion of the CTMNA or substituted CTMNA to AMNC or substituted AMNC. such time being varied depending on several factors such as amount of CTMNA or substituted CTMNA to be treated and temperature. A sufficient amount of time to convert reactant to product is readily determined by routine experimentation. When the pyrolysis is performed at 280° C., the pyrolysis is carried out for a time greater than about one hour, preferably greater than about 24 hours. AMNC or substituted AMNC can be recovered and purified using conventional methods such as distillation, crystallization, and chromatography.

The major product of the pyrolysis, which is AMNC or substituted AMNC, can be represented by the formula:

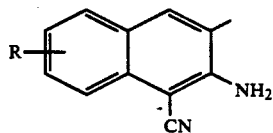

wherein R is as described above. Most preferably. R is hydrogen.

The yield of AMNC or substituted AMNC from the pyrolysis of CTMNA or substituted CTMNA will vary widely with reaction conditions such as temperature and time of reaction. Typically, yield is greater than about 80 percent. Preferably, yield is greater than about 90 percent.

In the pyrolysis of starting material, ethylene is also produced. Ethylene is also a useful compound, such as in the manufacture of polyethylene. Ethylene can be recovered and separated from other products of the pyrolysis by conventional techniques.

AMNC or substituted AMNC can be used as an analytical reagent to test for the presence of aldehydes. Thus, AMNC or substituted AMNC can be reacted with an aldehyde to form an imine. This process can be carried out neat or with an organic solvent at varying temperatures. Temperature varies depending on the reactivity of the particular aldehyde and can be any temperature at which AMNC or substituted AMNC form an imine with the aldehyde to be tested. Typically, the temperature is in the range from about 25° C. to about 200° C. Essentially any aldehyde can be used in this invention so long as at least a portion of the aldehyde is capable of forming an amine when reacted with AMNC. Simple aldehydes having no other functional groups are useful as well as aldehydes substituted with various functional groups.

The following examples are provided to illustrate this invention. All weights and percentages are by weight unless indicated otherwise.

EXAMPLE 1

Preparation of CTMNA

SAN copolymerization is carried out by thermal polymerization at about 155° C. in a continuous stirred tank reactor. A syrup is obtained from the polymerizer contained 55 percent polymer (25 percent acrylonitrile units in the polymer). The syrup is continuously pumped into an evacuated (less than 10 mmHg) tank heated at 240° C. Molten polymer is pumped from the bottom of the tank. The volatile components are passed through a condenser heated at 100° C. where the least volatile components (trimers) were condensed to form a trimer syrup. The trimer syrup is characterized using gas chromatography, high pressure liquid chromatography, $^1$H NMR. and $^{13}$C NMR. and is found to consist of 70 percent by weight CTMNA.

Preparation of AMNC

One gram of trimer syrup is placed in a thick-walled glass ampoule having an i.d. of 0.25 inch, an o.d. of 0.5 inch, and a length of 8 inches. The ampoule is next evacuated and sealed. The ampoule is heated in a sand bath at 280° C. for two days. The ampoule is removed, cooled to ambient temperatures, and the end containing a dark brown pyrolysate is further cooled until it is too viscous to flow readily. Next, the other end of the ampoule is frozen to liquid nitrogen temperatures whereby a solid is deposited at the end that is frozen to liquid nitrogen temperatures. Finally, the tube is opened, and the frozen solid is dissolved in CDCL$_3$. An analysis of the sample in CDCl$_3$ is performed and shows the frozen solid to be ethylene by $^1$H NMR and $^{13}$C NMR.

The pyrolysate is flash chromatographed on 60 angstrom 230–400 mesh silica gel with hexane:ethyl acetate 10:1. and is programmed up to a hexane:ethyl acetate volume ratio 4:1. The amber AMNC fraction is repeatedly recrystallized from chloroform until the crystals (melting point of 102° C.) and the mother liquor are very pale yellow. The purified AMNC has an intense UV spectrum with $\lambda_{max}$ at 340 and 365 nm.

EXAMPLE 2

Preparation of the Imine Adduct of AMNC and Benzaldehyde

Ten mg of AMNC (0.055 mmol) prepared in EXAMPLE 1 are dissolved in 100 mg of benzaldehyde (1 mmol) and the resulting solution is heated for 16 hours on a hot plate at 100° C. Analysis of the resulting product is performed using a variety of techniques (HPLC-UV, GC-MS, $^1$H NMR, AND $^{13}$C-NMR) that show a 1:1 mixture of AMNC and the imine adduct (a 50 percent yield). excess benzaldehyde having been evaporated. The solid 1:1 AMNC:imine product is dissolved in methylene chloride and analyzed by HPLC-UV. The structure of the highly UV absorbing and fluorescing imine, represented the by the formula:

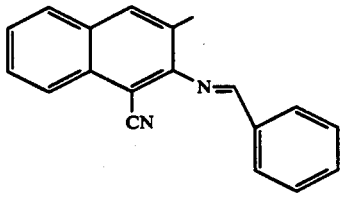

is corroborated by $^1$H and $^{13}$C NMR, and by GC/mass spectroscopy.

What is claimed is:

1. A process for producing 2-amino-3-methyl-1-naphthalenecarbonitrile) or substituted 2-amino-3-methyl-1-naphthalenecarbonitrile, comprising heating 4-cyano-1,2,3,4-tetrahydro-α-methyl-napthaleneacetonitrile or substituted 4-cyano-1,2,3,4-tetrahydro-α-methyl-1-naphthaleneacetonitrile represented by the formula:

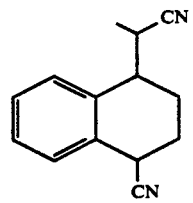

wherein R is alkyl of from 1 to 6 carbon atoms, halogen, cyano, or hydrogen under conditions effective to produce an 2-amino-3-methyl-1-naphthalenecarbonitrile or substituted 2-amino-3-methyl-1-naphthalenecarbonitrile and ethylene wherein 2-amino-3-methyl-1-naphthalenecarbonitrile or substituted 2-amino-3-methyl-1-naphthalenecarbonitrile is represented by the formula:

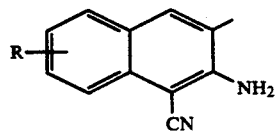

wherein R is alkyl of from 1 to 6 carbon atoms, halogen, cyano, or hydrogen.

2. The process of claim 1 wherein R is hydrogen.

3. The process of claim 1 wherein the temperature is greater than about 250° C. and less than about 350° C.

4. The process of claim 1 wherein the yield of 2-amino-3-methyl-1-naphthalenecarbonitrile or substituted (AMNC) 2-amino-3-methyl-1-naphthalenecarbonitrile is greater than about 90 percent.

5. The process of claim 1 wherein the process is conducted under an inert atmosphere.

* * * * *